(12) United States Patent
Oravecz et al.

(10) Patent No.: US 7,522,780 B2
(45) Date of Patent: **\*Apr. 21, 2009**

(54) FREQUENCY DOMAIN PROCESSING OF SCANNING ACOUSTIC IMAGING SIGNALS

(75) Inventors: Michael G. Oravecz, Naperville, IL (US); Lei Pen, Aurora, IL (US); Lawrence W. Kessler, Buffalo Grove, IL (US); Zhiqu Guo, Prospect Heights, IL (US)

(73) Assignee: Sonoscan, Inc., Elk Grove Village, IL (US)

( * ) Notice: Subject to any disclaimer, the term of this patent is extended or adjusted under 35 U.S.C. 154(b) by 768 days.

This patent is subject to a terminal disclaimer.

(21) Appl. No.: 11/088,668

(22) Filed: Mar. 24, 2005

(65) Prior Publication Data

US 2005/0240106 A1    Oct. 27, 2005

Related U.S. Application Data

(62) Division of application No. 10/007,984, filed on Nov. 13, 2001, now Pat. No. 6,890,302.

(60) Provisional application No. 60/248,138, filed on Nov. 13, 2000.

(51) Int. Cl.
G06K 9/40 (2006.01)

(52) U.S. Cl. .................. 382/260; 382/255; 382/280; 600/407

(58) Field of Classification Search ............... 600/443, 600/437, 445; 73/105, 588, 597, 599, 602, 73/606, 619, 620
See application file for complete search history.

Primary Examiner—Long V Le
Assistant Examiner—Saurel J Selkin
(74) Attorney, Agent, or Firm—Husch Blackwell Sanders Welsh & Katz

(57) ABSTRACT

Method and apparatus useful in the inspection of a target comprises scanning the target with a pulsed acoustic beam, sensing the pulsed beam after it has been modified by interaction with the target, producing a time-domain signal indicative of the modifications, processing the time-domain signal to produce a frequency domain representation of the modifications, and producing an image-wise display of the frequency domain representation of the modifications. In one execution disclosed, the frequency domain representation is altered and then reconverted to a time domain signal before display.

77 Claims, 3 Drawing Sheets

FREQUENCY DOMAIN PROCESSING OF SCANNING ACOUSTIC IMAGING SIGNALS

CROSS-REFERENCE TO RELATED APPLICATION

This application is a utility application based upon, and deriving priority from, Provisional Application Ser. No. 60/248,138, filed Nov. 13, 2000 which is owned by the owner of the present application.

BACKGROUND OF THE INVENTION

In a standard scanning acoustic microscope, a target is scanned with a high energy multi-megahertz acoustic beam pulsed at kilohertz rates. The beam as it passes through or is reflected from the target is modified in amplitude and/or phase.

The target may be inspected at various internal interfaces for defects by collecting, amplifying and appropriately time-gating a reflected fraction of the input signal. A greater gate delay represents a deeper reflected level in the target.

The most typical displays produced using this gated return signal will show greater amplitude signals where the acoustic probe at the gated depth is more strongly reflected than at other levels. By way of example, a strong reflection will occur if a disbond between two layers of an IC package has created an air gap, air being highly reflective of acoustic waves traveling through a semiconductor medium.

Scanning acoustic microscopes utilizing such information displays have proven to be of great benefit in nondestructive inspection and testing of semiconductor packages and many other commercial articles and laboratory targets. To generate as much information as possible from the sensed acoustic beam, many image enhancements techniques have been developed—colorization of differentiated information, edge enhancement, and so forth. Yet the desire for more and different information about internal details in inspected targets continues to be intense and unabated.

OBJECTS OF THE INVENTION

It is an object of the present invention to provide a method and apparatus for extracting valuable information from the output of a scanning acoustic microscope which is not generated using known techniques.

It is another object to provide such method and apparatus which is of high resolution and accuracy.

It is still another object of the invention to provide such method and apparatus which is relatively inexpensive, and can be employed in real time or with stored information.

It is yet another object to provide such method and apparatus which correlates spatially with standard scanning acoustic microscope imagery and can therefore be employed as an image enhancing technique.

DESCRIPTION OF THE PREFERRED EXECUTIONS

Figure 1:
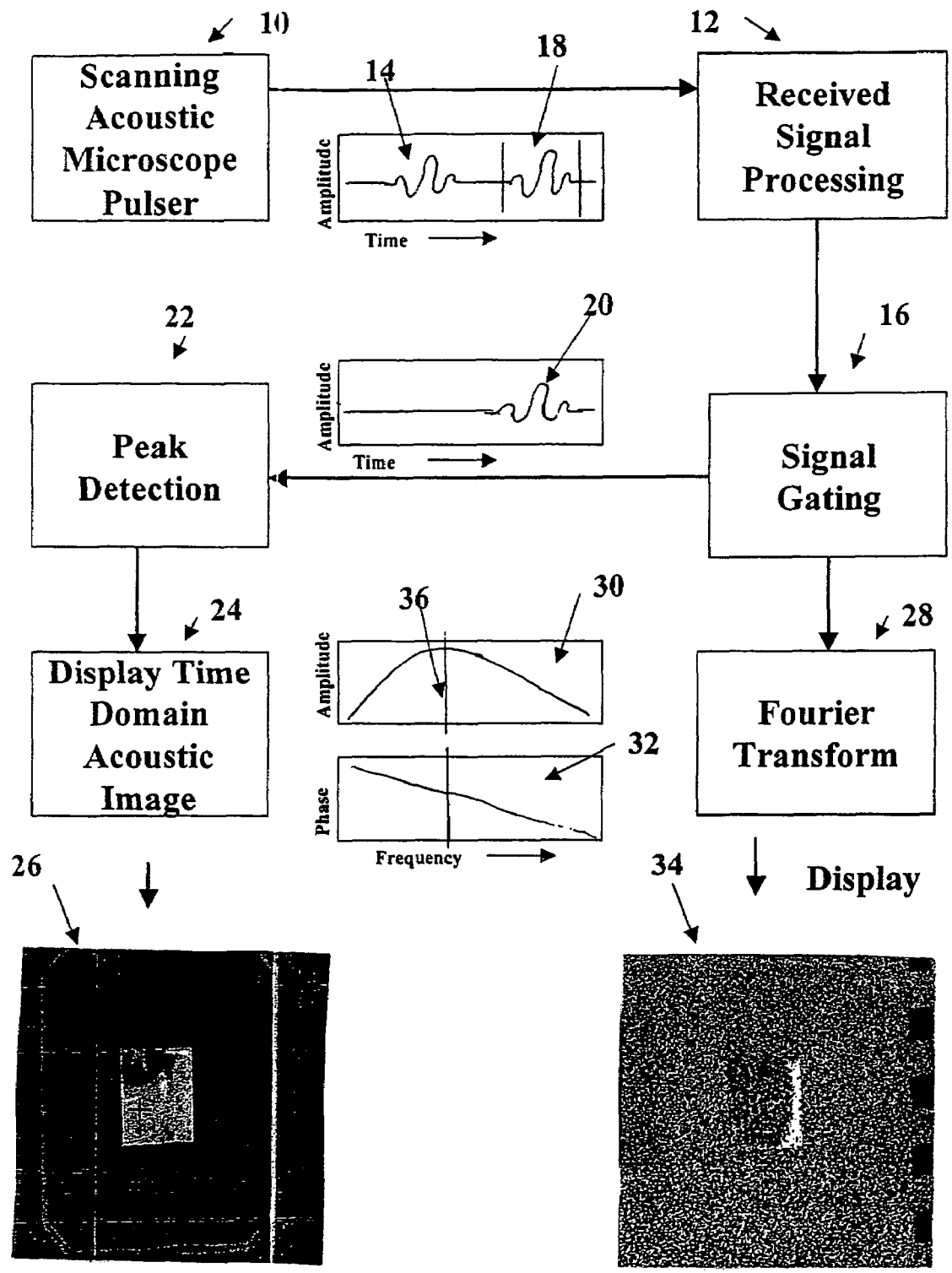
FIGS. 1-3 are schematic diagrams depicting three improved methods of processing acoustic microscope signals according to the teachings of the present invention.

FIG. 1 is a schematic diagram illustrating a preferred execution of a method aspect of the invention adapted for processing signals derived from a scanning acoustic microscope pulser 10.

As is well known in the art a scanning acoustic microscope typically comprises a transducer which is driven by sharp voltage pulses which may have amplitudes of 100 volts or more and are typically in the frequency range of tens of megahertz to 100 megahertz or higher.

The pulsed acoustic beam penetrates the target, which may be an IC package, for example. A fraction of the energy passes through the target, and the remainder is absorbed or scattered. In many applications sufficient energy is returned to the transducer (after a delay) to be sensed. Acoustic energy is almost totally reflected by an air gap. Thus acoustic microscopes have proven to be extremely useful in locating disbonds (air gaps) between internal layers of a device such as an IC package.

The return signal is an amplitude signal composed of a range of frequencies centered around the transducer's resonant frequency. FIG. 1 shows a receiver 12 adapted to sense and amplify the acoustic signal returned from the target. The time domain signal after processing by the receiver 12 has a waveform which resembles that sketched at 14. The time domain signal 14 is representative of amplitude variations in the returned acoustic pulses at the pixel level.

As is well known in the art, the time domain signal 14 is conventionally gated by a gating process shown schematically at 16. During the gating process, a gate 18 isolates a pixel-representative signal segment associated with a single pixel. The gated waveform showing only the gated segment of the signal 14 is shown at 20.

Gating of the signal permits the user to examine any chosen level in the target simply by selecting an appropriate delay time for the gate. For example, a single pixel segment might be captured with a gate 100 nanoseconds wide set at a delay of 384-484 nanoseconds. If a deeper level were to be visualized a longer delay would be employed.

The waveform shape of the signal segment 20 characterizes modifications in the reflected amplitude of a particular acoustic pulse or pulses impinging on a pixel of the target. The modification may by caused by absorption, scattering, reflection, interference or other effects and its capture in the signal segment 20 is highly useful to those interested in a target's internal construction, defects and the like.

In accordance with standard practice in scanning acoustic microscopy, the gated pixel-wise signal segment 20 is subjected to a peak detection step 22 and then is displayed as a time domain acoustic image (see step 24 in FIG. 1). A standard time domain acoustic image is shown at 26. In the image at 26, the target is an IC package; the darkened area in the upper left corner indicates a disbond where the reflected acoustic energy is significantly higher than in the remaining areas of the target.

In a broad sense the present invention is directed to a method of processing a time-domain signal derived from an acoustic microscope, comprising converting the signal to a frequency domain representation of the signal. More particularly, with reference to FIG. 1, the gated output time domain signal segment 20 is subjected to a frequency domain conversion step, preferably a Fourier transform, fast Fourier transform, discrete Fourier transform or other such well known signal processing systems with windowing functions (see step 28 in FIG. 1).

Two outputs may be developed by the Fourier transform step—an amplitude versus frequency waveform, sketched at 30, and a phase versus frequency waveform, sketched at 32.

In accordance with an aspect of the present method, an output from the Fourier transform step 28 is visually reproduced, as shown at 34. The information content of the frequency domain characterization of the pixels (one of which is under discussion here) is in many cases dramatically different from that produced by a time domain visualization. This can be noted even in the poorly reproduced pictures shown at 26 (time domain) and 34 (frequency domain). The pictures 26 and 34 are taken from successful laboratory tests.

It must be understood that the particular waveforms 20, 30 and 32 are each associated with a particular chosen pixel, whereas the time domain image 26 and the frequency domain image 34 are images of the entire target or some macro portion thereof.

In accordance with the present invention, two methods are offered for selecting the frequency components of the signal which are to be visualized in the frequency domain representation. FIG. 1 depicts one of the methods wherein in the frequency domain waveforms 30, 32, a single frequency (indicated at 36 on waveform 30) is selected. This may be accomplished with Windows™ software which facilitates selection of the particular chosen frequency under the control of a mouse.

The particular frequency 36 selected may, for example, be at the peak of the pixel-wise amplitude versus frequency waveform 30 as shown. That selected frequency then becomes the frequency component which is visualized for all pixels in the display. Thus as the chosen frequency 36 is varied along the frequency axis of signal segment 20, the visual appearance of the image 34 may change dramatically, indicating that the acoustic reflections from the target may vary widely at a particular target depth with the particular frequency being studied.

The frequency domain information alone is proving to be very valuable in providing clues to hidden structures and anomalies within a target. By simultaneously displaying both time domain and frequency domain signals side by side or superimposed, still further information can be derived concerning the target internal structures and anomalies. This subject will be discussed further in connection with the method of FIG. 2.

The particular site on the target where the determinate pixel of interest is located is preferably determined through Windows™ software which places a cursor under mouse or keyboard control at any desired location on the target.

Figure 2:
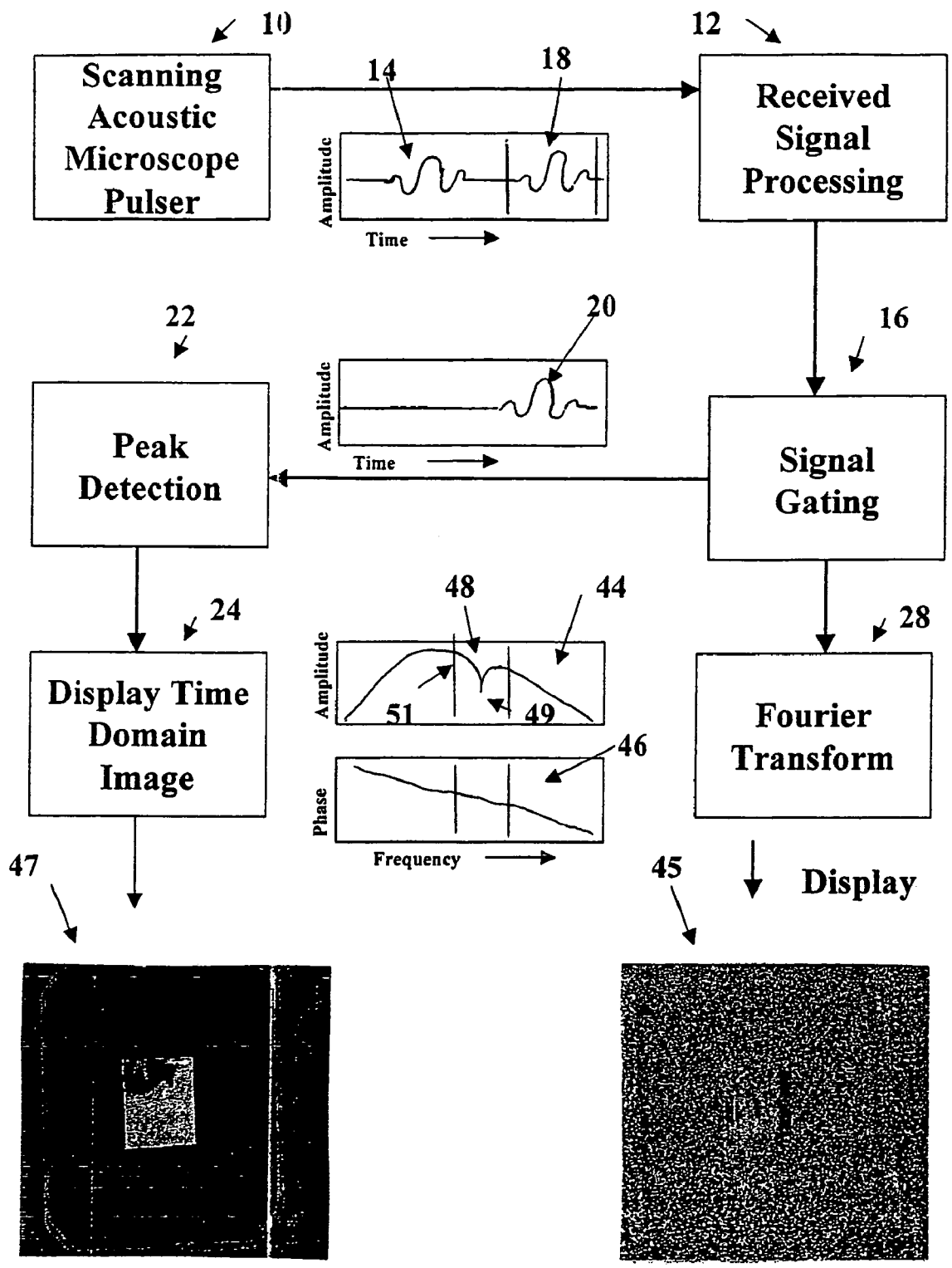

A second method of implementing the principles of the invention is depicted schematically in FIG. 2. It is noted that the same reference numerals appearing in different figures indicates like structure and function. Thus the FIG. 2 method may be the same as the FIG. 1 method described above except for the method step of selecting the frequency component of the frequency domain waveform to be visualized.

Again, as in the FIG. 1 method, the output of the Fourier transform step 28 may comprise an amplitude versus frequency waveform 44 and a phase versus frequency waveform 46. However, rather than selecting a single frequency to be visualized for the chosen pixel and all pixels (that is, image-wise), a band 48 of frequencies is selected. The width and location of the band on the waveform 44 is preferably varied using Windows™ software which permits under mouse or keyboard control, varying of the location and width of the band 48 delimiters.

Thus the user may choose at will the width and location of the band of frequencies to be visualized. He might be interested in embracing a range of frequencies across the peak of the amplitude versus frequency waveform. If the entire waveform is compressed at one of the spectrum for example, he may wish to embrace the entire band of frequencies. Having selected the band and its location, in accordance with a step of the present invention (not shown), an algorithm is chosen which will produce a single valued output in the application of the chosen band of frequencies to each pixel in the target to be processed and displayed. The algorithm may, for example, average the amplitudes of the frequencies in the band, or choose the lowest value in the band 48 (see point 49 on waveform 44) or the highest amplitude value in the band (see point 51 on the waveform 44).

The waveform 44 is illustrated as having a curious dip within the chosen band 48 of frequencies for the selected pixel. This is the type of information which likely would not be revealed in a rendition of a conventional peak-detected time domain signal. What might cause such a dip? If the target included two closely spaced and parallel interfaces reflected acoustic waves could interfere constructively and destructively. Interference would occur at certain frequencies and not at others. Thus the phenomenon is frequency selective.

With a broad band of reflected frequencies as normally occurs, the particular band or bands of frequencies affected, and the distances in the target corresponding to multiples of their wavelengths, could signify valuable interface spacing or other information. Thus the dip in the band 48 could signify that interference is occurring in the span of frequencies across the dip.

If one pixel or pixel group has a dip as described and an adjacent pixel or pixel group does not, this fact may be shown in an image-wise frequency domain display as an area of high contrast. The ability to visualize or otherwise develop information about a target's internal structure or anomalies which are undetectable using standard time domain imaging is one of advantages of Fourier transform signal processing according to the invention.

In FIG. 2, image 47 is a conventional time domain rendition of the target using conventional image processing as described. Image 45 is a frequency domain image produced using the Fourier domain conversion techniques described, and using a band of frequencies rather that a single frequency as in the FIG. 1 method. The visual differences in the two images are manifest, indicating the presence of new information in the frequency domain image than is not present in the time domain image.

Figure 3:
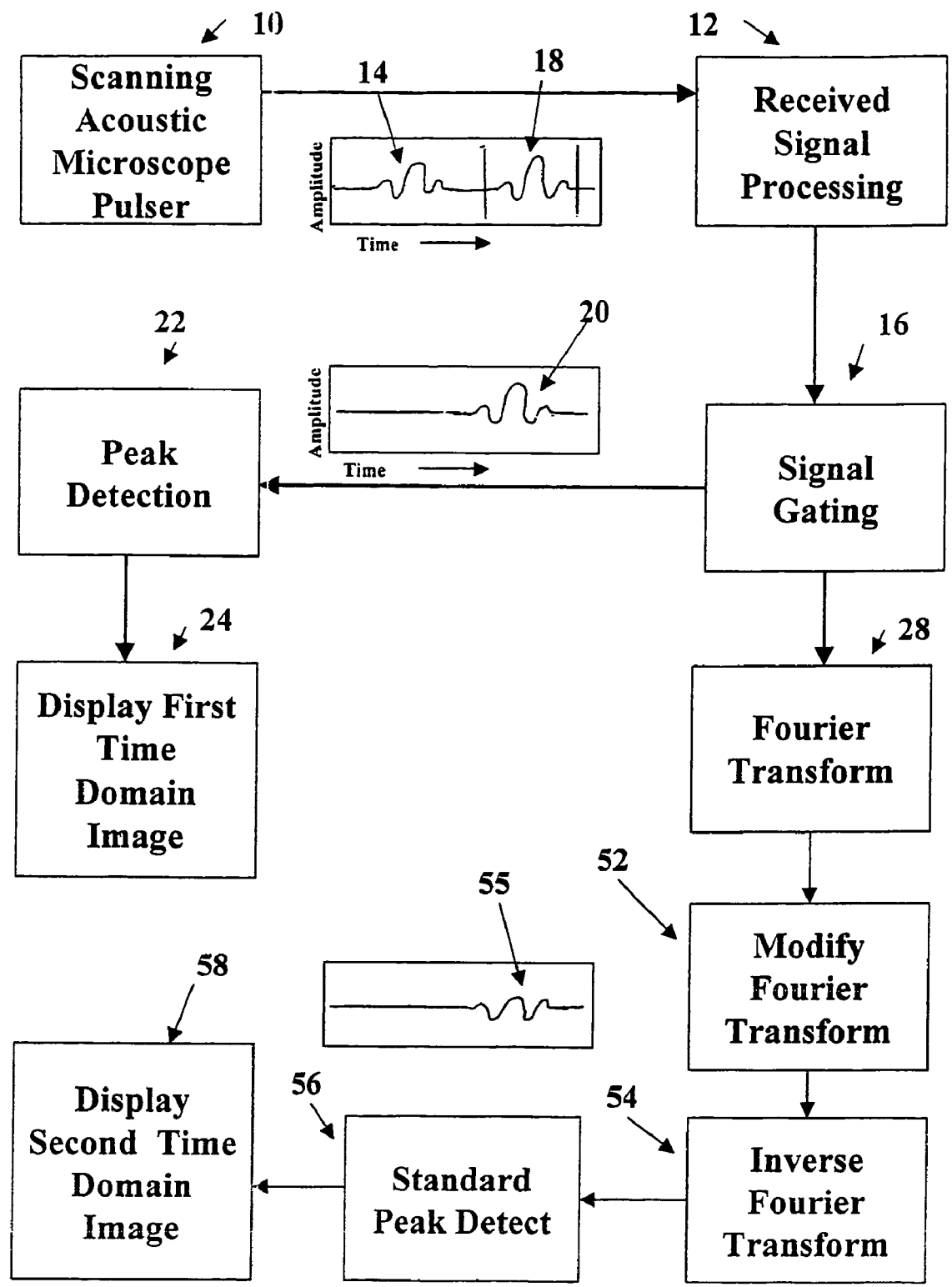

A third execution of the principles of the invention is depicted in FIG. 3, where again the use of like reference numerals denotes like structure and function. In the FIG. 3 execution, rather than processing and displaying the frequency domain output from the Fourier transform step 28 directly, its output is instead modified (step 52), as by any desired shading, apodizing or other filter function, for example, and then processed in an inverse Fourier transform step 54.

The output of the inverse Fourier transform step 54 is a gated time domain signal 55 which will have the general appearance of a gated time domain signal, but will differ from the gated time domain signal 20 derived from the pulser 10, receiver 12 and gating 16 steps, as a result of the predetermined filter function used to process the frequency domain characterization of the pixel signal.

Thus each of the three executions of the invention described operate on the frequency spectrum of an examined sample pixel—the first two methods by the selection for display of the frequency component (single frequency or band of frequencies). The FIG. 3 method contemplates a more sophisticated or aggressive (than simply gating) phase and/or amplitude filtering of the spectrum of frequencies in the return beam from the examined sample location.

Whereas the preferred executions of the invention have been described in a method context, one skilled in the art will be cognizant of the systems and software necessary to carry out the described methods and this description is intended to embrace those structures.

Other alternatives and embodiments are contemplated. For example, the outputs from the Fourier transform step 28 in the FIGS. 1 and 2 executions could also be inverse transformed and displayed as time domain signals. The pulser signal could be stored or processed in real time. Executions of the principles of the invention other than those described are within the scope of the present invention and are intended to be embraced by the following claims.

What is claimed is:

1. An acoustic micro imaging method useful in the inspection of a target, comprising:
    scanning the target with a focused pulsed acoustic beam;
    sensing the pulsed beam after it has been modified by interaction with the target and producing a time-domain signal indicative of the modifications; and
    processing said time-domain signal to produce a frequency domain representation of frequency selective modifications to the pulsed acoustic beam produced by said interaction with said target, said frequency domain representation further comprising a plurality of pixels where each pixel's brightness is amplitude modulated by a phase component of the sensed pulsed beam from a respective portion of the target.

2. The method defined by claim 1 including inverse transforming said frequency domain representation.

3. The method defined by claim 2 including modifying said time-domain signal before processing it.

4. The method defined by claim 2 including modifying said frequency domain representation before said inverse transforming operation.

5. The method defined by claim 4 wherein said modifying comprises apodizing, shading, or otherwise filtering said frequency domain representation.

6. The method defined by claim 1 wherein said processing comprises Fourier transforming.

7. The method defined by claim 6 including inverse Fourier transforming said frequency domain representation.

8. An acoustic micro imaging method useful in the inspection of a target, comprising:
    scanning the target with a focused pulsed acoustic beam;
    sensing the pulsed beam after it has been modified by interaction with the target and producing a time-domain signal indicative of the modifications;
    processing said time-domain signal to produce a frequency domain representation of frequency selective modifications to the pulsed acoustic beam produced by said interaction with said target; and
    producing an image-wise display of said frequency domain representation of the modifications, said image-wise display further comprising a plurality of pixels where each pixel's brightness is amplitude modulated by a phase component of the sensed pulsed beam from a respective portion of the target.

9. The method defined by claim 8 including simultaneously producing an image-wise display of said time-domain signal.

10. The method defined by claim 9 including inverse transforming said frequency domain representation to a time-domain signal, and wherein said image-wise display of said time-domain signal displays the result of said inverse transforming.

11. An acoustic micro imaging method useful in the inspection of a target, comprising:
    scanning the target with a focused pulsed acoustic beam;
    sensing the pulsed beam after it has been modified by interaction with respective portions of the target and producing a time-domain signal indicative of the modifications;
    gating the signal segment to isolate a pixel-representative segment thereof;
    converting the gate-isolated signal segment to a frequency domain representation of frequency selective modifications to the pulsed acoustic beam produced by said interaction with said target, in the frequency domain of the signal;
    identifying a selected frequency component of the signal; and
    producing an image-wise signal representing many pixels in an image wherein the information in the pixel-representative signal segment associated with each of said many pixels' brightness is amplitude modulated by a phase value of the said selected frequency component modified by the respective portion of the target.

12. The method defined by claim 11 including inverse transforming said frequency domain representation.

13. The method defined by claim 11 including producing an image-wise display of said frequency domain representation.

14. The method defined by claim 11 including simultaneously producing an image-wise display of said time-domain signal.

15. The method defined by claim 14 including inverse Fourier transforming said frequency domain representation to a time-domain signal, and wherein said image-wise display of said time-domain signal displays the result of said inverse transforming.

16. The method defined by claim 12 including modifying said frequency domain representation before said inverse transforming operation.

17. The method defined by claim 16 wherein said modifying comprises apodizing, shading, or otherwise filtering said frequency domain representation.

18. The method defined by claim 11 wherein said converting comprises Fourier transforming.

19. A method of processing a time-domain signal derived from an acoustic microscope, comprising converting the signal into a frequency domain representation of the signal that shows frequency selective modifications to the signal caused by interaction of an acoustic signal with a target, said frequency domain representation further comprising a plurality of pixels where each pixel's brightness is amplitude modulated by a phase component of the sensed pulsed beam from a respective portion of the target.

20. The method defined by claim 19 including producing an image-wise display of said frequency domain representation.

21. The method-defined by claim 20 including simultaneously producing an image-wise display of said time-domain signal.

22. The method defined by claim 19 wherein said converting comprises Fourier transforming.

23. A method of processing a gated time-domain signal derived from a pulsed beam acoustic microscope, comprising Fourier transforming the signal to a frequency domain representation of the signal showing frequency selective modifications to the signal caused by interaction of an acoustic signal with a target, said frequency domain representation further comprising a plurality of pixels where each pixel's brightness is amplitude modulated by a phase component of the gated time-domain signal from a respective portion of the target.

24. A method of processing a time-domain signal derived from a scanning acoustic microscope, comprising:
   gating the signal to isolate a pixel-representative segment thereof;
   converting the signal into a frequency domain representation of the signal that shows frequency selective modifications to the signal caused by interaction of an acoustic signal with respective portions of a target;
   in the frequency domain of the signal, identifying a selected frequency component of the signal; and
   producing an image-wise signal representing many pixels in an image wherein the information associated with each of said many pixels' is amplitude modulated by a phase value of the said selected frequency component of the pixel-representative signal segment from a respective portion of the target.

25. The method defined by claim 24 including inverse transforming said frequency domain representation.

26. The method defined by claim 24 including modifying said frequency domain representation before said identification of a selected frequency component of the signal.

27. The method defined by claim 26 wherein said modifying comprising apodizing, shading, or otherwise filtering said frequency domain representation.

28. The method defined by claim 24 wherein said converting is a Fourier transform process.

29. The method defined by claim 24 wherein said frequency component comprises a single frequency.

30. The method defined by claim 29 including inverse transforming said frequency domain representation.

31. The method defined by claim 24 wherein said frequency component comprises a band of frequencies.

32. The method defined by claim 31 including inverse transforming said frequency domain representation.

33. The method defined by claim 31 wherein said step of producing includes determining the dominant frequency in said selected band of frequencies.

34. A method useful in the inspection of a target, comprising:
   scanning the target with a pulsed acoustic beam; sensing the pulsed beam after it has been modified by interaction with the target and producing a first time-domain signal indicative of the modifications;
   processing said time-domain signal to produce a frequency domain representation of frequency selective, phase modifications to the pulsed acoustic beam produced by said interaction with respective portions of said target;
   modifying said frequency domain signal using a predetermined filter function; and
   converting said modified frequency domain signal to a second time-domain signal, where said second time-domain signal further comprises a plurality of frequency components from the respective portions of the target that have been modified by the predetermined filter function.

35. The method defined by claim 34 including producing an image-wise display of said second time domain representation.

36. The method defined by claim 35 including simultaneously producing an image-wise display of said frequency representation.

37. The method defined by claim 34 wherein said converting comprises Fourier transforming.

38. The method defined by claim 34 including producing a simultaneous image-wise display of said first and second time-domain signals.

39. A method of processing a first time-domain signal derived from an acoustic microscope, comprising converting the signal into a frequency domain representation of the signal that shows frequency selective modifications to a phase of the signal caused by interaction of an acoustic signal with respective portions of a target, modifying the frequency domain representation of the signal using a predetermined filter function, and converting the modified signal to a second time-domain signal having a different image content than said first time-domain signal, where said second time-domain signal further comprises a plurality of phase versus frequency components from respective portions of the target that have been modified by the predetermined filter function.

40. The method defined by claim 39 wherein said modifying comprises apodizing, shading, or otherwise filtering said frequency domain representation.

41. The method defined by claim 39 including producing an image-wise display of said second time domain representation.

42. The method defined by claim 41 including simultaneously producing an image-wise display of said frequency representation.

43. The method defined by claim 39 wherein said converting comprises Fourier transforming.

44. The method defined by claim 39 including producing a simultaneous image-wise display of said first and second time-domain signals.

45. A method of processing a gated first time-domain signal derived from a pulsed beam acoustic microscope, comprising Fourier transforming the signal into a frequency domain representation of the signal that shows frequency selective modifications to a phase of the signal caused by interaction of an acoustic signal with respective portions of a target, modifying the frequency domain representation of the signal using a predetermined filter function, and inverse Fourier transforming the signal to a second time-domain signal having a different image content than said first time-domain signal, where said second time-domain signal further comprises a plurality of phase versus frequency components from the respective portions of the target that have been modified by the predetermined filter function.

46. A method of processing a first image-wise time-domain signal derived from an acoustic microscope, comprising:
   gating the signal to isolate a pixel-representative segment thereof;
   converting the signal into a frequency domain representation of the signal that shows frequency selective modifications to a phase of the signal caused by interaction of an acoustic signal with respective portions of a target;
   in the frequency domain of the signal, identifying a selected frequency component of the signal;
   modifying the frequency domain representation of the phase of the signal using a predetermined filter function; and
   inverse Fourier transforming the signal to produce a second image-wise time-domain signal representing many pixels in an image from respective portions of the target wherein the information in the pixel-representative signal segment associated with at least a number of said many pixels is amplitude modulated by respective phase versus frequency components within the pixel-representative segment and where said amplitude modulation has been altered due to said modification of said signal by the predetermined filter function while in the frequency domain.

47. The method defined by claim 46 wherein said modifying comprising apodizing, shading, or otherwise filtering said frequency domain representation.

48. The method defined by claim 46 wherein said converting is a Fourier transform process.

49. Apparatus for inspecting a target and producing a frequency domain representation of a gated time domain signal, comprising:
   a scanning acoustic microscope having an acoustic pulser that produces a focused, pulsed acoustic beam;
   a signal processor including an acoustic pulse sensor, amplifier and pixel gate coupled to said pulser that produces a time-domain representation of the acoustic beam after it has been modified by interacting with respective portions of the target; and
   a frequency domain converter responsive to the output of said signal processor that produces a frequency domain representation of phase selective modifications to the acoustic beam produced by said interacting with the target, said frequency domain representation further comprising a plurality of pixels where each pixel's brightness is amplitude modulated by a phase component of the sensed pulsed beam from a respective portion of the target.

50. The apparatus defined by claim 49 including inverse transform circuitry coupled to said frequency domain converter.

51. The apparatus defined by 49 wherein said converter is a Fourier transformer.

52. Apparatus useful in the inspection of a target, comprising:
   means for scanning the target with a pulsed acoustic beam;
   means for sensing the pulsed beam after it has been modified by interaction with the target and producing a time-domain signal indicative of the modifications;
   means for gating the signal to isolate a pixel-representative segment thereof;
   means for converting the signal into a frequency domain representation of the signal that shows phase selective modifications to the signal caused by interaction of an acoustic signal with respective portions of a target;
   means for identifying in the frequency domain a selected frequency component of the signal; and
   means for producing an image-wise signal representing many pixels in an image wherein the information in the pixel-representative signal segment associated with each of said many pixels' brightness is amplitude modulated by the phase of said selected frequency component from a respective portion of the target.

53. The apparatus defined by claim 52 including means for producing an image-wise display of said image-wise signal.

54. The apparatus defined by claim 53 including simultaneously producing an image-wise display of said time-domain signal.

55. The apparatus defined by claim 52 wherein said converting comprises Fourier transforming.

56. Apparatus useful in the inspection of a target, comprising:
   means for scanning the target with a pulsed acoustic beam;
   means for sensing the pulsed beam after it has been modified by interaction with the target and producing a first time-domain signal indicative of the modifications;
   means for processing said time-domain signal to produce a frequency domain representation of frequency selective modifications to a phase of the pulsed acoustic beam produced by said interaction with said target where said frequency domain representation is amplitude modulated by a phase of a frequency component of the sensed pulsed beam from a respective portion of the target;
   means for modifying said frequency domain signal using a predetermined filter function; and
   means for converting said modified frequency domain signal to a second time-domain signal.

57. The apparatus defined by claim 56 including means for producing an image-wise display of said second time domain representation.

58. The apparatus defined by claim 57 including means for simultaneously producing an image-wise display of said frequency representation.

59. The apparatus defined by claim 56 wherein said converting comprises Fourier transforming.

60. The apparatus defined by claim 56 including means for producing a simultaneous image-wise display of said first and second time-domain signals.

61. Apparatus for processing a first time-domain signal derived from an acoustic microscope, comprising
   means for converting the signal into a frequency domain representation of the signal that shows frequency selective modifications to a phase of the signal caused by interaction of an acoustic signal with respective portions of a target,
   means for modifying the frequency domain representation of the signal, and
   means for converting the modified signal of respective portions of the target to a second time-domain signal having a different image content than said first time-domain signal where said second time-domain signal further comprises a plurality of phase components that have been modified by the means for modifying.

62. The apparatus defined by claim 61 including means for producing an image-wise display of said second time domain representation.

63. The apparatus defined by claim 62 including means for simultaneously producing an image-wise display of said frequency representation.

64. The apparatus defined by claim 61 wherein said means for converting comprises Fourier transforming.

65. The apparatus defined by claim 61 including means for producing a simultaneous image-wise display of said first and second time-domain signals.

66. The method defined by claim 1 including modifying said time-domain signal before processing it.

67. The method defined by claim 66 wherein said modifying comprises windowing, shading, or otherwise filtering said time-domain signal.

68. The method defined by claim 31 wherein said step of producing includes determining the lowest amplitude in said selected band of frequencies.

69. The method defined by claim 38 including producing a third image-wise display of said frequency-domain representation prior to converting.

70. The method defined by claim 42 including producing a third simultaneous image-wise display of said first time-domain signal.

71. The method defined by claim 44 including producing a third simultaneous image-wise display of said frequency-domain representation.

72. The apparatus defined by claim 60 including means for producing a third simultaneous image-wise display of said frequency representation.

73. The apparatus defined by claim 65 including means for producing a third simultaneous image-wise display of said frequency representation.

74. The method defined by claim 1 including digitizing said time-domain signal before processing it.

75. The method defined by claim 66 including inverse transforming said frequency-domain representation.

76. The method defined by claim 11 including digitizing the gate-isolated signal segment prior to converting it.

77. The method defined by claim 68 including inverse transforming said frequency-domain representation.

* * * * *